(12) United States Patent
Chung

(10) Patent No.: US 11,116,956 B2
(45) Date of Patent: Sep. 14, 2021

(54) NEEDLE DISC ROLLER APPARATUS WITH PUMP

(71) Applicant: 3CP CO., LTD, Yongin-si (KR)

(72) Inventor: Yongkyun Chung, Seoul (KR)

(73) Assignee: 3CP CO., LTD

( * ) Notice: Subject to any disclaimer, the term of this patent is extended or adjusted under 35 U.S.C. 154(b) by 0 days.

(21) Appl. No.: 16/956,615

(22) PCT Filed: Mar. 12, 2019

(86) PCT No.: PCT/KR2019/002852
§ 371 (c)(1),
(2) Date: Jun. 22, 2020

(87) PCT Pub. No.: WO2019/182281
PCT Pub. Date: Sep. 26, 2019

(65) Prior Publication Data
US 2020/0376246 A1    Dec. 3, 2020

(30) Foreign Application Priority Data

Mar. 22, 2018 (KR) ........................ 10-2018-0033015

(51) Int. Cl.
*A61M 37/00* (2006.01)
*A61M 35/00* (2006.01)

(52) U.S. Cl.
CPC ...... *A61M 37/0015* (2013.01); *A61M 35/003* (2013.01); *A61M 2037/0023* (2013.01); *A61M 2037/0046* (2013.01); *A61M 2210/04* (2013.01)

(58) Field of Classification Search
CPC ............ A61M 35/003; A61M 37/0015; A61M 2210/04; A61M 2037/0023; A61M 2037/0046
(Continued)

(56) References Cited

U.S. PATENT DOCUMENTS

2010/0121307 A1    5/2010   Lockard et al.
2010/0292723 A1*   11/2010  Lee .................... A61H 15/0092
                                              606/180
(Continued)

FOREIGN PATENT DOCUMENTS

KR        20-0429555 Y1    10/2006
KR     10-2008-0100569 A    11/2008
(Continued)

OTHER PUBLICATIONS

International Search Report for PCT/KR2019/002852 dated Jun. 11, 2019 from Korean Intellectual Property Office.

*Primary Examiner* — Brandy S Lee
*Assistant Examiner* — Nidah M Hussain
(74) *Attorney, Agent, or Firm* — Nicholas Park

(57) ABSTRACT

A needle disk roller apparatus having a built-in pump, includes: a drug container (11) filled with a drug and having a built-in pump assembly (10); and a roller head (14) being able to interwork with the pump assembly (10), supplied with the drug by up-down pressing, configured to form holes in the skin using a plurality of needle disks (21) so that the drug penetrates into the skin, and having a drug base (16) that prevents the drug supplied from the pump assembly (10) from flowing down, and accumulates a predetermined amount of the drug inside an arcuate bottom (28) so that the drug is appropriately supplied to the needle disks 21 when the needle disks 21 are rotated.

7 Claims, 8 Drawing Sheets

(58) Field of Classification Search
USPC .......................................................... 604/173
See application file for complete search history.

(56) References Cited

U.S. PATENT DOCUMENTS

| | | | | |
|---|---|---|---|---|
| 2011/0250008 A1* | 10/2011 | Lim | .................... | B05B 11/3015 |
| | | | | 401/188 R |
| 2011/0319865 A1* | 12/2011 | Buss | .................. | A61M 5/3297 |
| | | | | 604/506 |
| 2015/0018797 A1* | 1/2015 | Waldman | .......... | A61M 5/31583 |
| | | | | 604/506 |
| 2015/0065950 A1* | 3/2015 | Banar | ................. | A61M 5/3287 |
| | | | | 604/46 |

FOREIGN PATENT DOCUMENTS

| | | | |
|---|---|---|---|
| KR | 10-2009-0060116 A | 6/2009 |
| KR | 10-1200669 B1 | 11/2012 |
| KR | 20-0471796 Y1 | 3/2014 |

\* cited by examiner

[FIG. 1A]
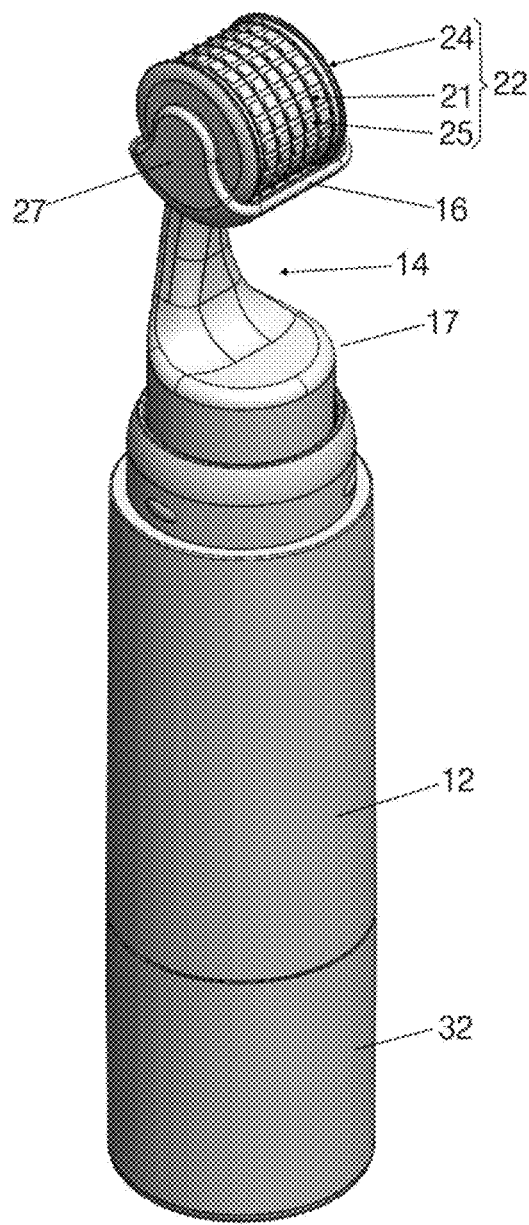

[FIG. 1B]
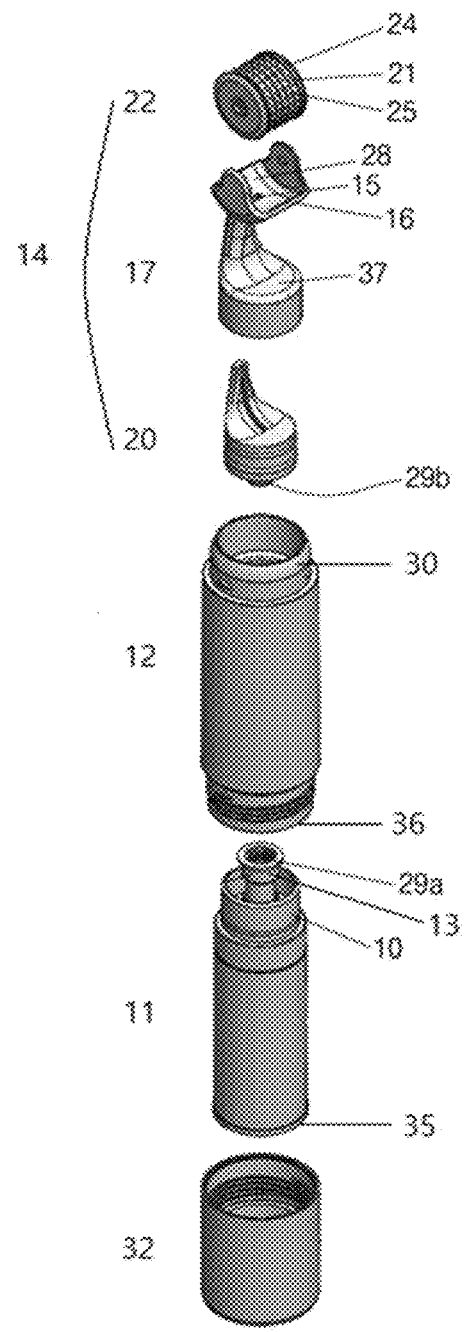

[FIG. 2]
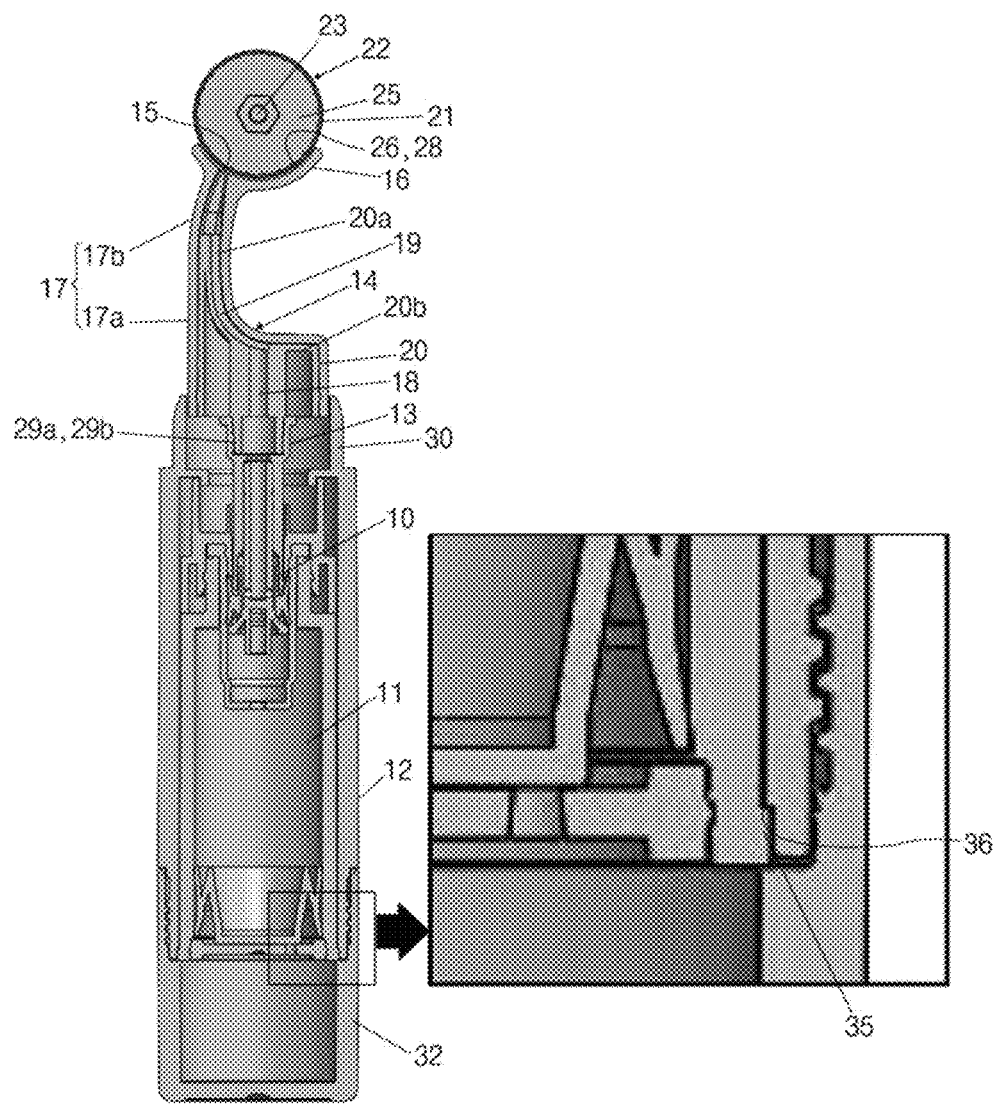

[FIG. 3]
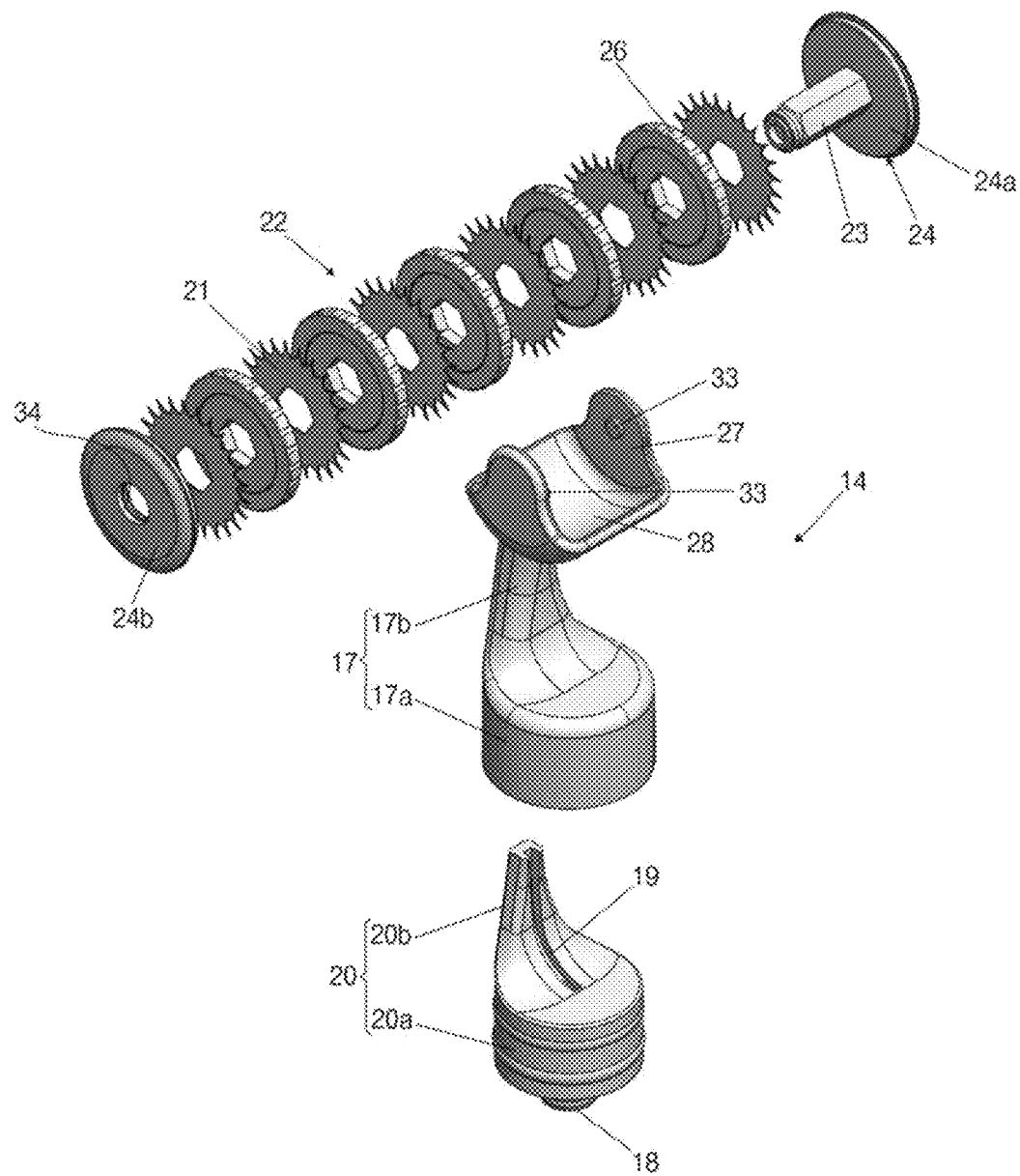

[FIG. 4]
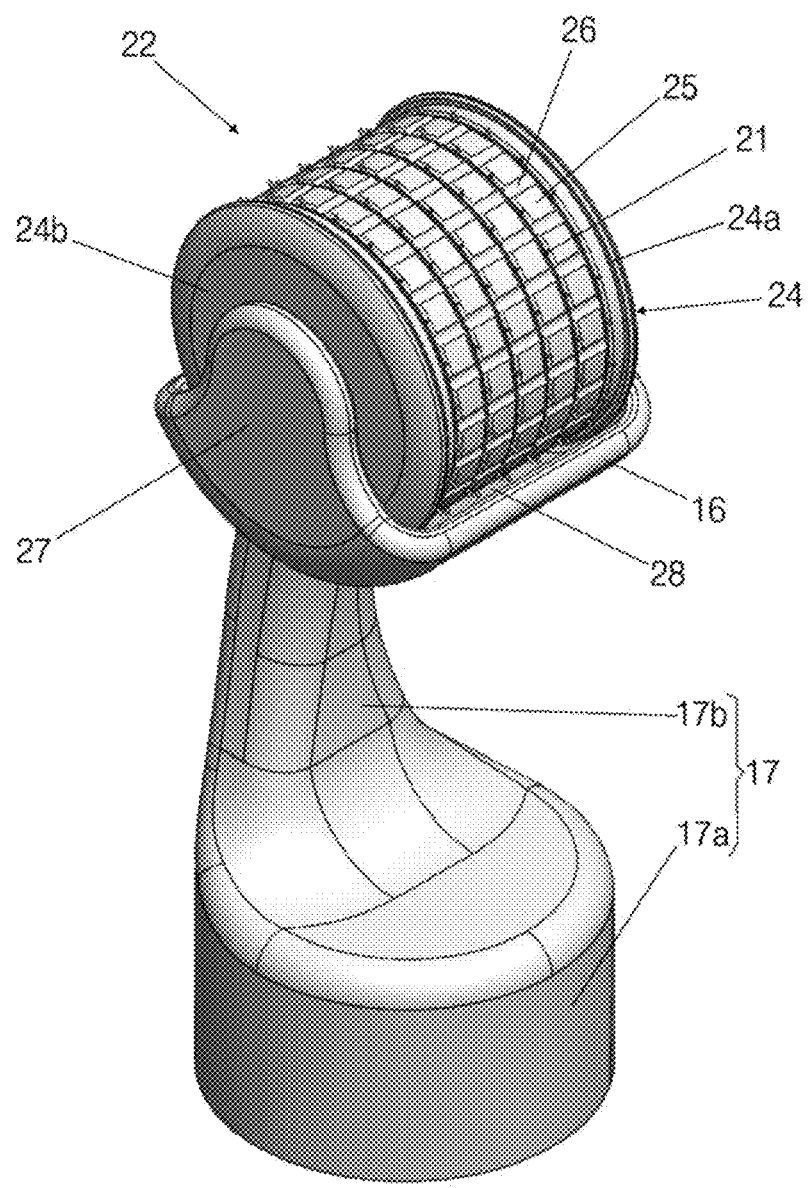

[FIG. 5]
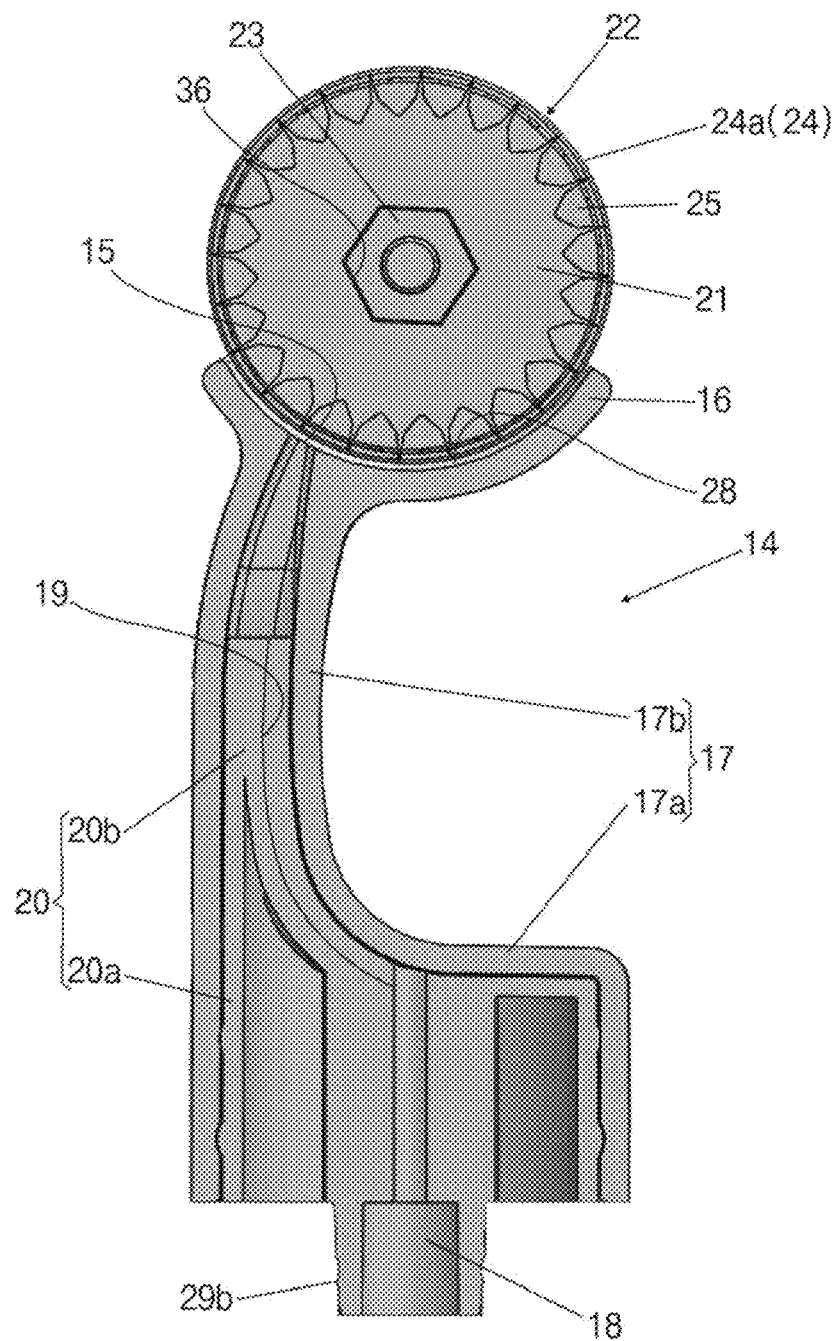

[FIG. 6]
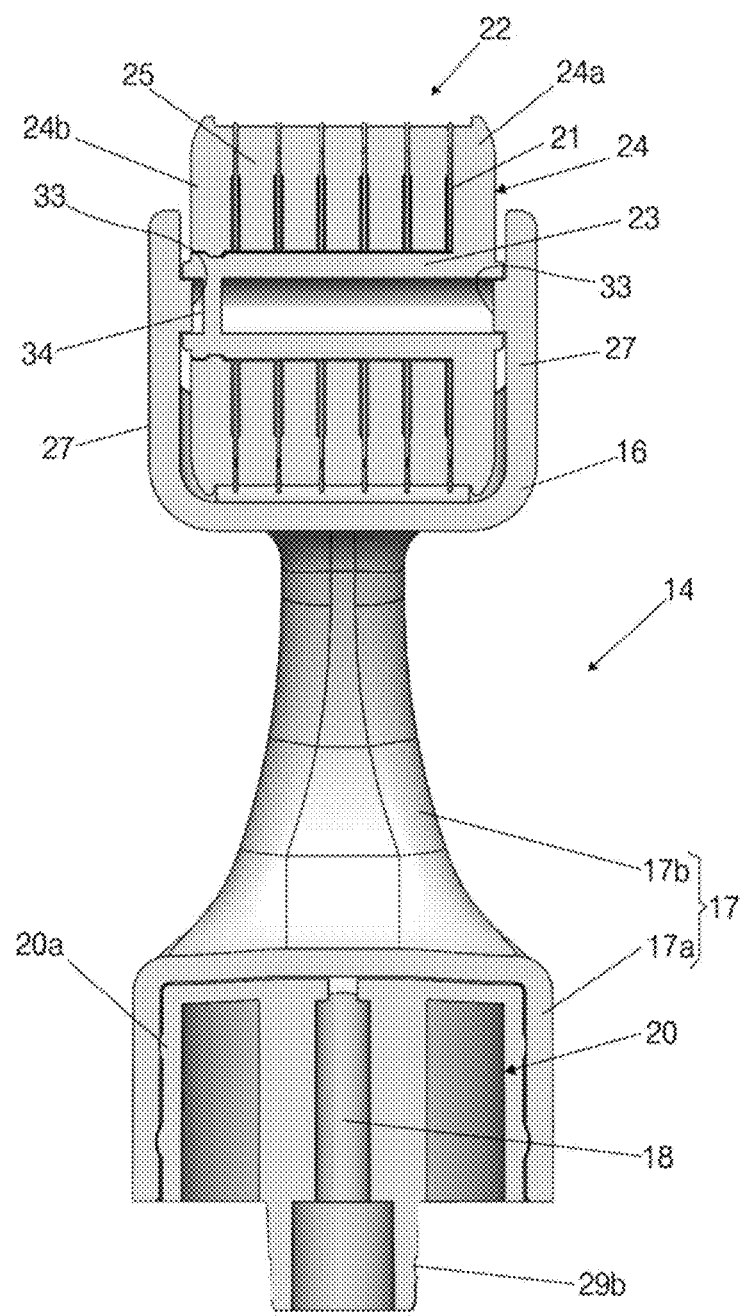

[FIG. 7]
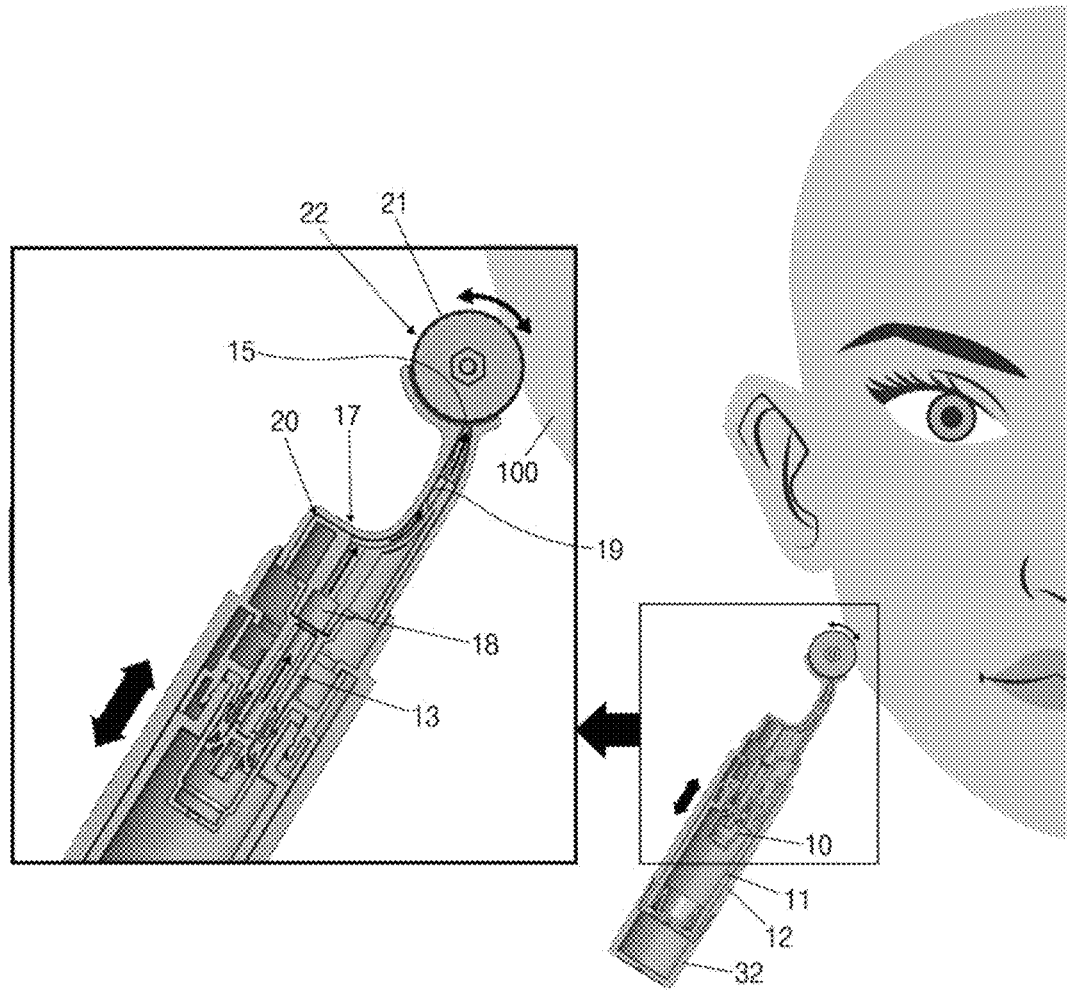

NEEDLE DISC ROLLER APPARATUS WITH PUMP

TECHNICAL FIELD

The present invention relates to a needle disk roller apparatus having a built-in pump and, more particularly, to a needle disk roller apparatus having a built-in pump, the needle disk roller apparatus used for skincare that enables a skin beauty liquid or a drug to penetrate into skin while bringing several needle disks in contact with the surface of the skin and forming holes in the skin.

BACKGROUND ART

In general, cosmetics or drugs that are applied to the skin to remove fine wrinkles and freckles, reduce skin pore size, improve skin tone, cure atopic skin, and reduce scarring due to acne and burns only remain in the horny layer of the skin without penetrating into the skin.

For example, the proportion of cosmetics or drugs that are absorbed into the skin is not more than 0.03 to 2% and the remainder stays on the keratin or epidermis and is washed away.

In consideration of this problem, recently, a skincare method using a so-called Micro-needle Therapy System (MTS), which is a concept that increases the penetrability of active ingredients of drugs or cosmetics by forming holes in the dermis with rotary micro-needles and helps produce collagen by stimulating the skin has been frequently used.

For example, there is a method of using an individual drug container and an individual needle-roller. This method is a hassle to use because it involves first applying a drug in the drug container at a desired portion and then rubbing it with the needle-roller or first applying a drug to a needle-roller and then rolling it. Further, there is the inconvenience of a drug not being evenly applied in rolling after being applied to the skin. Further, when a drug is directly applied to the needle-roller for use, the drug may run before it is applied on a desired portion.

As another example, there is a needle roller apparatus having a form in which a fine needle roller is coupled to the upper end of a drug container filled with a drug and a hole through which the drug can be discharged is formed between the drug container and the fine needle roller.

However, the drug supply method of the needle roller apparatus is a natural drip type, so that the apparatus is normally operated only when the drug part is positioned at the top and the needle roller is positioned at the bottom. Accordingly, a user can receive a procedure from another person while lying down, but a drug may run if the viscosity is low or it may be required to hit the drug container with a palm, etc., to discharge the drug if the viscosity is high. Further, when a user directly uses the apparatus, the face of the user must be raised, so that there is great inconvenience when individuals use the apparatus by themselves.

DISCLOSURE

Technical Problem

Accordingly, the present invention has been made to solve the inconvenience when a user directly uses and an objective of the present invention is to provide a needle disk roller apparatus having a built-in pump that any user can easily use while looking at a mirror by pumping a drug to the top and naturally supplying the drug to a needle disk of a roller head by simply pressing a finger touch portion of the roller head without the inconvenience, by completely removing the problem of the related art where a user has to invert an apparatus by positioning a drug part at the top even though a pump container filled with a drug is positioned at the bottom and a roller head including a plurality of needle disks is positioned at the top. Further, an objective of the present invention is to provide a new type of needle disk roller apparatus having a built-in pump, that enables economic use of a drug without the residual drug in a pump container through forcible pumping, and is able to be more economically and efficiently used by causing a predetermined amount of drug or skin beauty liquid to be discharged out of the pump container to be supplied to a needle disk roller in an amount as much a user wants while improving convenience for the user.

Technical Solution

To achieve the objectives, the needle disk roller apparatus having a built-in pump provided in the present invention has the following characteristics.

The needle disk roller apparatus having a built-in pump includes: a drug container filled with a drug and having a built-in pump assembly; a case accommodating the drug container; a roller head connected to a plunger of the pump assembly to interwork and coupled to an upper end of the case to be able to slide up and down to be supplied with the drug by an up-down pumping operation of the pump assembly by downward pressing; and a lower cap fixing and preventing the drug container having a built-in pump and sliding in a lower portion of the case accommodating the drug container from moving down when the drug container is pressed down, and providing comfortable gripping of a handle.

In particular, the roller head may include: a roller head body having a drug base having a drug outlet at an upper end, and coupled to the case; an inner socket core having a drug inlet fitted into a pump plunger of the drug container and fitted into the roller head body to form a drug channel connected to the drug outlet so that the drug is smoothly supplied; and a needle disk rotatably coupled to the drug base of the roller head body and forming holes in the skin using a plurality of needle disks so that the drug penetrates into the skin.

The needle disk may be composed of: a bobbin having a shaft and having a separable structure; and pluralities of annular spacers and needle disks coaxially fitted onto the shaft of the bobbin and alternately arranged.

A plurality of drug storage grooves may be axially formed and circumferentially arranged at regular intervals on circumferential surfaces of the annular spacers.

Further, the drug base of the roller head may have side arms at both sides to support the roller, and an arcuate bottom for storing the drug, and accordingly, the drug base can temporarily store the drug flowing inside through the drug outlet. Therefore, it is possible to prevent a drug or a skin beauty liquid from running to undesired portions before rolling.

The drug inlet of the inner socket core and the plunger of the pump assembly can detachably fitted to each other, and a lower circumference of the body of the roller head is inserted into a cylindrical guide tube formed at an upper end of the outer case, and thus the head body can be guided when sliding up and down.

As an exemplary embodiment, the drug container having the pump assembly therein can be stored and withdrawn in and from the outer case, so the entire drug container including the pump assembly can be replaced as a disposable product after the drug is completely used, so that the apparatus can be more sanitarily and conveniently used.

Advantageous Effects

The needle disk roller apparatus having a built-in pump provided in the present invention has the following effects.

First, by applying a new combination type of a pump and a needle disk roller in which a roller head including a plurality of needle disks is coupled to a drug container having a built-in pump, even though a user simply presses a finger touch portion of the roller head, an appropriate amount of a drug or a skin beauty liquid in the drug container can be pumped upward and uniformly distributed on the needle disks, so that it is possible to easily use. Further, it is possible to improve efficiency of skin care by improving the penetration effect of a drug and it is also possible to economically use by preventing the waste of a drug.

Second, a predetermined amount of drug can be supplied to the needle disks in one-time pumping, and the predetermined amount of drug pumped upward at one time can be stored in the roller head and continuously supplied to the needle disks, so that the drug can appropriately penetrate into the skin, thereby further improving a skin treatment effect.

Third, since the needle disk part including the needle disks and the roller is manufactured separately from the inner core part and then they are combined, the apparatus can be easily manufactured using a mold and manufacturing costs can be reduced. Accordingly, the manufacturing convenience of the entire apparatus can be improved.

Fourth, since the head assembly and the drug container having the pump are coupled in a one-touch male-female manner, the drug container can be easily replaced. Accordingly, anyone including a novice can conveniently use the apparatus.

Fifth, since the apparatus can be very easily handled, operated, and used, anyone can easily, simply, and effectively perform skin treatment (prescription) on him/herself even at home without going to a hospital or a special skincare clinic, it is possible to perform skin treatment without burdens in terms of cost and time.

Sixth, since the drug container having the pump assembly therein and being able to be stored and withdrawn in and from the case is a disposable product, the entire drug container can be replaced and used as a disposable product after the drug is completely used, so that the apparatus can be more sanitarily and conveniently used.

DESCRIPTION OF DRAWINGS

FIG. 1A is a perspective view showing a needle disk roller apparatus having a built-in pump according to an embodiment of the present invention.

FIG. 1B is an exploded view of FIG. 1A.

FIG. 2 is a cross-sectional view showing the needle disk roller apparatus having a built-in pump according to an embodiment of the present invention.

FIGS. 3 and 4 are perspective views showing a roller head of the needle disk roller apparatus having a built-in pump according to an embodiment of the present invention.

FIGS. 5 and 6 are cross-sectional views showing the roller head of the needle disk roller apparatus having a built-in pump according to an embodiment of the present invention.

FIG. 7 is a cross-sectional view showing a use state of the needle disk roller apparatus having a built-in pump according to an embodiment of the present invention.

BEST MODE

The present invention is described in detail with reference to the accompanying drawings.

FIGS. 1A, 1B, and 2 are perspective and cross-sectional views showing a needle disk roller apparatus having a built-in pump according to an embodiment of the present invention, and FIGS. 3 to 6 are perspective and cross-sectional views showing a roller head of the needle disk roller apparatus having a built-in pump according to an embodiment of the present invention.

In the following description, a drug means a liquid substance that is used for skin beauty such as a cosmetic, a functional cosmetic, a pharmaceutical, and means dense mucous cosmetics having predetermined viscosity such as serum, essence, concentrate, and booster of cosmetics and pharmaceuticals having similar viscosity and used in the dermatology department of hospitals.

As shown in FIGS. 1A to 6, the needle disk roller apparatus having a built-in pump is configured to be able to be easily used by anyone at home and increase the effect of skin treatment (prescription) by adopting a method, which supplies a drug to a needle disk using the power of a pump, and improving the structure of a roller head including a needle disk to improve the effect of permeation of a drug into the skin.

To this end, the needle disk roller apparatus having a built-in pump includes a drug container 11 as a means for supplying a drug required for skin treatment.

The drug container 11 is filled with a drug and a pump assembly 10, as a built-in structure, is disposed in the drug container 11.

The drug container 11, which is a cylindrical container for storing a predetermined amount of known drug that is applied to the skin for skin improvement and treatment, may be disposed in a case 12 to be described below.

The pump assembly 10 is installed in the drug container 11, and a plunger 13 (a drug outlet of the pump assembly 10 embedded in this way) may vertically protrude a certain distance from the center of the top of the drug container 11.

An upper end 29a of the plunger 13 of the pump assembly 10 and a lower end 29b of a drug inlet 18 of an inner socket core 20 may be fastened in a one-touch male-female manner.

Here, the pump assembly 10 may be a known pump that is used for cosmetic containers, and the structure or operation thereof will not be described in detail.

In particular, in the case of the drug container 11 including the built-in pump assembly 10, there is a feature of allowing arm disposable use by replacement with a new drug container after the drug contained therein is exhausted.

For example, the drug container 11 can be stored/withdrawn in/from the case 12 and the entire drug container 11 including the pump assembly 10 can be replaced by taking out the drug container 11 in which the drug was entirely exhausted through the lower end of the case 12 and the putting a new drug container 11 filled with the drug through the lower end of the case 12.

The needle disk roller apparatus having a built-in pump includes the case 12 as a means for receiving the drug container 11.

The case 12 is a long cylindrical container and the cylindrical drug container 11 can be inserted into the case 12.

That is, when the drug container 11 is inserted and pushed up through an open bottom of the case 12, the drug container 11 can be fitted while sliding on the inner wall side of the case 12.

In particular, the present invention provides a structure that enables the drug container 11 to be easily mounted and removed and mounted at an accurate position.

To this end, a stepped portion 36 having a stepped structure is formed on the inner circumference of the lower end of the case 12 and a flange 35 is formed on the outer circumference of the lower end of the drug container 11.

Accordingly, when the drug container 11 is completely inserted through the bottom of the case 12, the flange 35 of the drug container 11 is seated and caught on the stepped portion 36 of the case 12. Therefore, the drug container is no longer inserted and can be mounted at the accurate position without moving further upward.

When the drug container 11 is mounted at the accurate position by locking action of the flange 35 and the stepped portion 36, the centers of the plunger 13 of the pump assembly 10 of the drug container 11 and the drug inlet 18 of the inner socket core 20 of a roller head 14 can be accurately aligned, so that it is possible to easily and conveniently replace the drug container 11 by simply fitting the drug container 11 into the case 12.

Further, the lower end of the drug container 11 mounted in the case 12 is pressed and supported by a lower cap 32 assembled to the lower end of the case 12, so that the drug container 11 can be maintained at the accurate position.

The lower cap 32 is coupled to the lower end of the case 12 in a screw-coupled manner, thereby fixing the drug container 11 embedded in the case 12 so that the drug container 11 cannot fall out, and improving overall gripping comfort when the apparatus of the present invention is used.

Further, the needle disk roller apparatus having a built-in pump includes the roller head 14 as a means that is supplied with a drug by a pumping operation of the pump assembly 10, and applies the drug while forming fine holes in the skin of a user.

The roller head 14 is connected to the pump assembly 10 to operate together, and accordingly, when the roller head 14 is moved up and down, the pump assembly 10 can supply the drug in the drug container 11 to the roller head 14 by pumping the drug.

The roller head 14 is divided into three parts of a needle disk roller 22, a body 17 having a drug base and a finger touch portion and connecting the drug container, and an inner socket core 20 of the body for smooth supply of a drug. The needle disk roller 22 will be separately described and the body of the roller head has a cylindrical body portion 17a and a hollow neck 17b integrally extending upward from a side of the upper end of the body portion 17a.

The body portion 17a of the roller head body 17 can be slidably fitted into a guide tube 30 formed at the case 12.

For example, the lower end circumference of the body portion 17a of the roller head body 17 is inserted into the cylindrical guide tube 30 formed at the upper end of the case 12, and accordingly, when a user presses the finger touch portion 37 to slide the roller head 14 up and down, the body portion 17a can be guided within the guide tube 30. As a result, a predetermined amount of drug can be accurately supplied to the needle disk roller through a drug outlet 15 of the roller head body by user's pumping operation.

Further, the inside of the neck 17b of the roller head body 17 may communicate with the drug outlet 15 of the drug base 16 to be described below.

The drug base 16 capable of accommodating a predetermined amount of drug while having the drug outlet 15 is integrally formed at the upper end of the roller head body 17, that is, the upper end of the neck 17b.

In particular, the drug base 16 has side arms 27 at both sides to hold both sides of the needle disk roller 22 and connects the lower ends of the side arms 27, thereby having a structure with a bottom 28 having a concave arcuate cross-section for temporarily storing a drug.

Here, the bottom 28 of the drug base 16 is formed in an arc shape having a curvature similar to the curvature of the circular needle disk roller 22, that is, the curvature of the needle disk 21 and an annular spacer 25, and is coaxially disposed under the needle disk 21 and the annular spacer 25. A predetermined gap may be formed between the bottom 28 and circumferential surfaces of the needle disk 21 and the annular spacer 25.

Accordingly, a predetermined amount of a drug introduced through the drug inlet 18 formed at the bottom 28 of the drug base 16 is filled inside the arcuate bottom 28. Further, the drug filled in this way can be uniformly applied to the circumferential surfaces of the needle disk 21 and the annular spacer 25 of the rotating needle disk roller 22.

As a result, a drug can be appropriately supplied to the needle disk roller 22 as a predetermined amount of drug always remains inside the bottom 28 by pumping one time.

Further, in addition to storing a predetermined amount of drug, the arcuate bottom 28 can naturally guide the drug discharged by pumping pressure inward, so that the discharge force of the drug can be offset. Accordingly, it is possible to prevent a waste of the drug and contamination due to the drug flying in all directions.

Pins 33 protrude from the facing inner sides of the side arms 27 of the drug base 16. The pins 33 are fitted into pin grooves 34 formed in a bobbin 24 of the roller 22, thereby functioning as the rotational center axis of the bobbin 24.

The roller head 14 includes the inner socket core 20 as a means for guiding the flow of a drug that is supplied to the needle disk 21 from the pump assembly 10.

The inner socket core 20 is formed in a similar shape to the roller head body 14, for example, it is composed of a cylindrical hollow core body portion 20a with an open bottom and a core neck 20b integrally extending upward from a side of the upper end of the core body portion 20a.

The drug inlet 18 having a vertical tube shape is integrally formed at the center inside the core body portion 20a of the inner socket core 20, and the lower end of the drug inlet 18 communicates with the upper end of the plunger 13 of the pump assembly 10.

That is, the outer circumferential surface of the lower end 29b of the drug inlet 18 and the inner circumferential surface of the upper end 29a of the plunger 13 are fastened in a one-touch male-female manner, and thus the drug inlet 18 and the plunger 13 can be connected to each other, and accordingly, the drug discharged from the plunger 13 can flow into the drug inlet 18.

As described above, since the drug inlet 18 of the inner socket core 20 and the plunger 13 of the pump assembly 10 are connected to each other in a male-female coupling structure by the upper end 29a and the lower end 29b, it is possible to easily replace the entire drug container 11 having the pump assembly 10 simply by separating or connecting the plunger 13 by separating or re-fastening the upper end 29a and the lower end 29b, which is a male-female coupling portion, when replacing the drug container 11.

A drug channel 19 is continuously formed longitudinally at the outer surface of the neck 10b of the inner socket core 20 while having a groove-shaped lower end section communicating with the drug inlet 18. The drug channel 19 can form a path through which a drug can move in cooperation with the arcuate inner wall side of the body portion 17a of the roller head body 17 when the inner socket core 20 is inserted into the roller head body 17.

Accordingly, a drug flowing in the drug inlet 18 of the inner socket core 20 flows through the drug channel 19, is guided upward, and then can flow out of the drug base 16 through the drug outlet 15 communicating with the upper end section of the drug channel 19.

The inner socket core 20 can be inserted and fitted into the roller head body 17.

That is, the core neck 20b of the inner socket core 20 can be tightly fitted to the neck 17b of the roller head body 17 and the core body portion 20a of the inner socket core 20 can be tightly fitted to the roller head body 17.

Here, when the inner socket core 20 and the roller head body 17 are coupled, it is preferable to apply a locking structure that uses a groove and a protrusion at the contact area to secure a close coupling state between the inner socket core 20 and the roller head body 17

In this way, since the inner socket core 20 and the roller head body 17 are separately formed and coupled in a mutually assembled manner, it is possible to easily manufacture using a mold without difficulty in design and production such as separation of a mold and reduce manufacturing costs, so that the manufacturing convenience of the entire apparatus can be improved.

The roller head body 17 includes the needle disk roller 22 as a means for actually forming holes in skin and enabling a drug to penetrate into the skin.

The needle disk roller 22 is disposed inside the drug base 16 of the roller head body 17, has a rotatable structure, and forms holes in the skin using a plurality of needle disks 21 so that a drug penetrates into the skin.

The needle disk roller 22 includes not only the bobbin 24 that functions as a support, but also a plurality of annular spacers 25 and a plurality of needle disks 21.

The bobbin 24 functions to group the annular spacers 25 and the needle disks 21 into the form of an assembly and has a cylindrical bobbin body portion 24a having a shaft 23 and a circular bobbin cap portion 24b coupled to the end of the shaft 23 in a screw-coupled manner.

Pin grooves 34 into which the pins 33 formed on both side arms 27 of the drug base 16 are fitted are formed at the outer surfaces and the centers of the ends of the bobbin body portion 24a and the shaft 23. Accordingly, the bobbin 24 can be supported by the drug base 16 by the pin grooves 34 and the pins 33 fitted to each other, and can rotate about both pins 33 as a central axis.

The shaft 23 of the bobbin body portion 24a has a polygonal shaft shape, for example, a hexagonal shaft shape, and hexagonal hole-shaped centers of the annular spacers 25 and the needle disks 21 can be fitted onto the hexagonal shaft 23.

As another example, a key groove (not shown) may be formed on the shaft 23 of the bobbin body portion 24a in the longitudinal direction of the shaft, and keys (not shown) of the annular spacers 25 and the needle disks 21 can be fitted into the key groove.

At this time, preferably, at least one pair of key grooves may be formed and arranged at regular intervals along the circumference of the shaft.

The needle disks 21, which are disk-shaped needles having a center hole and made of a thin metal material, have serrated needles formed on the circumferential surface of the disks to be able to form holes in the skin.

The needle disks 21 are coaxially fitted onto the shaft 23 of the bobbin 24 using the center holes, and can rotate with the bobbin 24 in this state.

Here, the center holes of the needle disks 21 are polygonal holes corresponding to the polygonal shaft 23, for example, hexagonal holes, and accordingly, the needle disks 21 fitted onto the shaft 23 do not idly spin on the shaft 23.

As another example, the keys (not shown) corresponding to the key groove (not shown) of the shaft 23 are formed in the center holes of the needle disk 21 and the keys are fitted into the key grooves, and thus the needle disks 21 do not idly spin on the shaft 23.

The annular spacers 25 are disks having a center hole and made of synthetic resin and are coaxially fitted onto the shaft 23 of the bobbin 24 using the center holes, so that the annular spacers 25 can rotate with the bobbin in this state and are positioned between the needle disks 21, thereby maintaining the gaps of the needle disks 21.

The center holes of the annular spacers 25 are polygonal holes corresponding to the polygonal shaft 23, for example, hexagonal holes, and accordingly, the annular spacers 25 fitted onto the shaft 23 do not idly spin on the shaft 23.

As another example, keys (not shown) corresponding to the key groove (not shown) of the shaft 23 are formed into the center holes of the annular spacers 25 and the keys are fitted into the key grooves, and thus the annular spacers 25 do not idly spin on the shaft 23.

In particular, several drug storage grooves 26 are axially formed and circumferentially arranged at regular intervals on the circumferential surfaces of the annular spacers 25.

Accordingly, the drug storage grooves 26 of the annular spacers 25 are filled with the drug in the drug base 16, the drug in the drug storage grooves 26 can be supplied to the needle disks 21 at both sides of each of the annular spacers, and the drug supplied to the needle disks 21 is gradually applied to a the skin without running. Therefore, a drug can sufficiently penetrate into the holes formed in the skin by the needle disks 21.

That is, as a drug can be continuously supplied to the needle disk 21 from the drug storage grooves 26 of the annular spacers 25 disposed between the needle disks 21, the drug can sufficiently penetrate into skin while holes are formed in the skin by the needle disks 21.

FIG. 7 is a cross-sectional view showing a use state of the needle disk roller apparatus having a built-in pump according to an embodiment of the present invention.

As shown in FIG. 7, the needle disk roller apparatus having a built-in pump can be used as a method of forming holes in skin by rotating the needle disks 21 against the skin and simultaneously putting a drug into the skin.

First, when the finger touch portion 37 of the body 17 of the roller head 14 is pressed down, the plunger 13 of the pump assembly 10 is pressed and a predetermined amount of drug in the drug container 11 is pumped by the pump assembly 10.

Next, a predetermined amount of the drug pumped by the pump assembly 10 accumulates inside the bottom 28 of the drug base 16 after sequentially passing the drug inlet 18, the drug channel 19, and the drug outlet 15 through the plunger 13.

Next, the drug accumulated inside the bottom 28 of the drug base 16 is applied not only to the needle disks 21, but also to the annular spacers 25 by rolling of the needle disk roller.

In this state, when a user holds the case 12 and the lower cap 32 connected to the case 12 by hand and rolls the needle disks 21 of the needle disk roller 22 up and down against the skin 100 such as the skin of the face, the needle disks 21 form holes in the skin 100 while rotating, and simultaneously, the drug applied to the needle disks 21 penetrates into the skin 100, and thus treatment for skin problems can be achieved.

Further, when the pumped drug is almost exhausted, by repeating the pumping operation again, it is possible to continuously supply the drug, form holes in the skin, and put the drug into the skin.

Since it is possible to manage the skin through the simple pumping operation for drug supply and the operation of forming holes in the skin with the needle disks and putting a drug into the skin while the needle disk roller is upright, anyone can easily use the apparatus. Further, it is possible to simply manage the skin at home without going to a hospital or an expert and the drug in the drug container can be economically used to the last drop through forcible pumping by the pump.

As described above, the present invention provides a new type of needle disk roller apparatus having a built-in pump, and thus it is possible to easily use the apparatus and increase satisfaction in skin care by improving the penetration effect of a drug. Further, its benefits include not only that it can be used economically by preventing waste of drugs and that it has excellent manufacturing efficiency but also that it can promote convenience in terms of usability and can easily be used at home by anyone. Therefore, anyone can directly and simply perform skin treatment (prescription) without the burden of cost and time and spatial constraints such as at home.

DESCRIPTION OF THE REFERENCE NUMERALS IN THE DRAWINGS

10: pump assembly
11: drug container
12: case
13: plunger
14: roller head (needle disk, body, inner socket core)
15: drug outlet
16: drug base
17: body
18: drug inlet
19: drug channel
20: inner socket core
21: needle disk
22: needle disk roller
23: shaft
24: bobbin
25: annular spacer
26: drug storage groove of body
27: side arm
28: bottom of drug base
29a, 29b: one-touch fitting portion
30: guide tube
32: lower cap
33: pin
34: pin groove
35: flange
36: stepped portion
37: finger touch portion

The invention claimed is:

1. A needle disk roller apparatus having a built-in pump configured to press drug upward airlessly, comprising:

a drug container (11) filled with a drug and having a built-in pump assembly (10), wherein the built-in pump assembly is configured to trigger the drug container (11) airlessly by pressing downward causing the drug to be supplied upward; and a roller head (14) being able to interwork with the pump assembly (10), supplied with the drug by up-down pressing, configured to form holes in the skin using a plurality of needle disks (21) so that the drug penetrates into the skin, and having a drug base (16) that prevents the drug supplied from the pump assembly (10) from flowing down, and accumulates a predetermined amount of the drug inside an arcuate bottom (28), wherein the roller head (14) includes an inner socket core (20) which forms a drug channel (19) communicating with a drug outlet (15) in a roller head body (17) by being coupled inside the roller head body (17) while having the drug outlet (15) formed in the drug base (16) at an upper end and having a drug inlet (18) connected to a plunger (13) at a lower end, wherein the arcuate bottom (28) having concave arcuate cross-section and located between the needle disks (21) and the roller head body (17) configured to form predetermined gap so that the drug is appropriately supplied, and the upper end of the drug outlet (15) is located vertically above to the center of the arcuate bottom (28) configured to store a predetermined amount of drug and apply to the circumferential surface of needle disks (21) when the needle disks (21) are rotated.

2. The needle disk roller apparatus of claim 1, wherein the drug base (16) of the body (17) of the roller head (14) has side arms (27) at both sides to support the needle disk roller (22).

3. The needle disk roller apparatus of claim 2, wherein the needle disk roller (22) includes a plurality of annular spacers (25), and a plurality of drug storage grooves (26) are axially formed and circumferentially arranged at regular intervals on circumferential surfaces of the annular spacers (25) so that the drug supplied to the needle disk roller is gradually applied to a surface of the skin without running to be efficiently used in rolling.

4. The needle disk roller apparatus of claim 1, comprising a case (12) configured to accommodate the drug container (11) having the built-in pump assembly (10), wherein a stepped portion (36) having a stepped structure is formed on an inner circumference of a lower end of the case (12) and a flange (35) is formed on an outer circumference of a lower end of the drug container (11) so that the drug container (11) is mounted at an accurate position by locking between the flange (35) and the stepped portion (36) when the drug container (11) is inserted into the case (12).

5. The needle disk roller apparatus of claim 4, comprising a lower cap (32) which prevents the drug container (11) from being fallen out in the case (12) by the up-down pressing.

6. The needle disk roller apparatus of claim 1, wherein a lower circumference of the roller head body (17) is inserted into a cylindrical guide tube (30) formed at an upper end of the case (12) so that the roller head body (17) is guided when sliding up and down.

7. The needle disk roller apparatus of claim 1, wherein the drug container (11) including the built-in pump assembly (10) is mounted to be capable of being stored and withdrawn in and from the case (12) so that the entire drug container

(11) including the pump assembly (10) is replaced and used when the drug is completely used.

* * * * *